United States Patent [19]

Morganson et al.

[11] 4,409,415

[45] Oct. 11, 1983

[54] OLEFIN OLIGOMERIZATION USING BORON TRIFLUORIDE AND AN ALCOHOL-POLYOL COCATALYST

[75] Inventors: Neal E. Morganson, McCandless Township, Allegheny County; Adam V. Vayda, Oakmont Borough, both of Pa.

[73] Assignee: Gulf Research & Development Company, Pittsburgh, Pa.

[21] Appl. No.: 303,369

[22] Filed: Sep. 18, 1981

[51] Int. Cl.³ .......................... C07C 3/02; C07C 3/18
[52] U.S. Cl. .................................. 585/525; 585/511; 585/521
[58] Field of Search ................ 585/525, 511, 521

[56] References Cited

U.S. PATENT DOCUMENTS

| | | | |
|---|---|---|---|
| 3,382,291 | 5/1968 | Brennan | 585/525 |
| 3,997,621 | 12/1976 | Brennan | 585/525 |
| 4,045,507 | 8/1977 | Cupples et al. | 585/511 |

FOREIGN PATENT DOCUMENTS

| | | | |
|---|---|---|---|
| 734498 | 8/1955 | United Kingdom | 585/525 |

*Primary Examiner*—Delbert E. Gantz
*Assistant Examiner*—A. Pal
*Attorney, Agent, or Firm*—Deane E. Keith; Forrest D. Stine; Donald L. Rose

[57] ABSTRACT

Olefin oligomers suitable as lubricants are prepared with a catalyst comprising boron trifluoride and a mixture of an alcohol, and a polyol. 1-Decene is oligomerized to a liquid product having an improved trimer to tetramer ratio using boron trifluoride and a mixture of n-butanol, and ethylene glycol.

8 Claims, No Drawings

OLEFIN OLIGOMERIZATION USING BORON TRIFLUORIDE AND AN ALCOHOL-POLYOL COCATALYST

SUMMARY OF THE INVENTION

Olefins are oligomerized using a three-component catalyst combination comprising boron trifluoride and a mixture of an alcohol and a polyol. When 1-decene is oligomerized using boron trifluoride and a liquid mixture of n-butanol and ethylene glycol, the resulting liquid oligomer is produced in good yield with an improved trimer to tetramer ratio.

DESCRIPTION OF THE INVENTION

Oligomers of certain 1-olefins are highly useful in preparing functional fluids such as lubricants, hydraulic fluids, transmission fluids, transformer fluids, and the like, generally compounded with other functional fluid components including appropriate additives. Each functional fluid product and generally the base fluid from which it is prepared must conform with established viscosity and volatility specifications. These alpha-olefin oligomer products are generally prepared by the cationic polymerization of the 1-olefin using a Friedel-Crafts catalyst, preferably boron trifluoride. The oligomer product is then hydrogenated in a conventional manner to stabilize the oligomer against oxidation and degradation.

In recent years 1-decene oligomer mixtures have been widely used in engine lubricant and hydraulic fluid formulations. Using conventional reaction conditions, the 1-decene polymerization reaction prepares a mixture of the oligomers including the dimer, trimer, tetramer, and pentamer comprising branched-chain molecular structures in which the branches are of relatively long carbon length. The dimer is removed for separate use to avoid volatilization loss from functional fluids comprising the higher oligomers. Minor amounts of oligomers higher than the pentamer, such as the hexamer, may be present but since their analysis and separation from the pentamer is difficult, they, if present, are generally reported as pentamer.

The composition of the oligomer mixture that is obtained from the oligomerization reaction is generally too rich in the tetramer and pentamer fractions to meet the viscosity specifications for desired formulations. This usually requires the separation of the oligomer composition into one or more product fractions comprising the trimer or a mixture of oligomers, rich or predominating in the trimer, depending on the particular need. And most significantly, this generally results in a significant unusable surplus of the higher oligomer fractions to be discarded, namely, the tetramer and pentamer fractions, as reported in U.S. Pat. No. 3,997,627. As a result those working in this field have directed their efforts towards increasing the selectivity of the 1-decene oligomerization reaction to the trimer, often referred to as improving the trimer to tetramer ratio or the ratio of the trimer to the heavier fractions.

The catalyst generally recommended for the oligomerization of 1-olefins is boron trifluoride and a liquid cocatalyst. The boron trifluoride must be present in molar excess of the cocatalyst for optimum results. A variety of substances have been used or suggested for use as the cocatalyst including water, various alcohols, ethers, polyols, aliphatic carboxylic acids, anhydrides, esters, and ketones, all of which are specified for this use in U.S. Pat. No. 4,045,507.

We have discovered that the combination of boron trifluoride catalyst together with a mixture of certain cocatalyst substances, and more specifically a mixture of an alcohol and a polyol, beneficially affects the oligomerization reaction and also benefits the resulting oligomer product. For example, when 1-decene is oligomerized using boron trifluoride, and this two-component cocatalyst combination, both the conversion and the trimer to tetramer ratio are improved.

The alcohol which is suitable in our cocatalyst mixture is an aliphatic alcohol having from one to about ten carbon atoms or a mixture thereof, preferably from about two to about four carbon atoms. This alcohol is used in the amount of about 75 to about 99 weight percent, preferably about 85 to about 98 percent of the total cocatalyst combination. Suitable alcohols include methanol, ethanol, propanol, isobutanol, n-decanol and the like. The preferred alcohols are the two to four carbon alcohols, and the most preferred alcohol is n-butanol.

The polyol which is used in our cocatalyst combination is selected from ethylene glycol, propylene glycol, butane diol, glycerine, and the like. A two or three carbon diol is preferred. The polyol or mixture of polyols are present in the amount of about one to about 25 weight percent, preferably about two to about 15 percent of the total cocatalyst combination.

The cocatalyst mixture can be used in a catalytic amount such as from about 0.01 to about 3.0 weight percent of the olefin undergoing oligomerization, preferably from about 0.1 to about 1.0 weight percent.

The oligomerization reaction is carried out using the three-component catalyst described herein and using conventional reaction conditions and procedures. Thus, the oligomerization can be carried out as a batch reaction as described in U.S. Pat. No. 3,780,128 or it can be carried out as a continuous reaction such as described in U.S. Pat. No. 4,045,507. Other types of oligomerization reactors and reaction systems are also suitable for use with our novel catalyst system. In general, any equipment or production layout designed for oligomerization with boron trifluoride catalyst can be used with our catalyst.

The oligomerization reaction is conducted within the temperature range of between about $-20°$ C. to about $90°$ C. with a temperature within the range of between about $20°$ C. and about $70°$ C. being preferred. The partial pressure of boron trifluoride in the oligomerization reactor is broadly maintained within the range of between about five and about 500 psig or higher, with a range of between about 20 and about 100 psig being preferred.

The olefins which can suitably be oligomerized by the novel catalyst described herein have between about six and about 20 carbon atoms, preferably between about 10 and about 14 carbon atoms. The olefins can be straight-chain or branched-chain olefins and can be alpha-olefins or internal olefins. The preferred olefins are normal alpha-olefins. When olefins having more than 13 carbon atoms are oligomerized, the dimer may be the preferred oligomer fraction.

DESCRIPTION OF A PREFERRED EMBODIMENT

Examples 1 and 2

1-Decene was oligomerized in an experiment using boron trifluoride and a cocatalyst mixture comprising n-butanol and ethylene glycol. This experiment was carried out at steady state conditions by the continuous process described in U.S. Pat. No. 4,045,507 using two stirred tank reactors in series. The results were compared with a substantially identical experiment using n-butanol alone. The operating conditions and product analyses are set out in the Table.

TABLE

| Example | 1 | 2 |
|---|---|---|
| Cocatalyst, wt % | | |
| n-butanol | 100 | 97 |
| eth. glycol | 0 | 3.0 |
| Cocat. conc., wt % | 0.56 | 0.40 |
| $BF_3$, conc., wt % | 0.63 | 0.53 |
| Temperature, °C. | 49–52 | 48–50 |
| Pressure, psi | 20 | 20 |
| Product, wt % | | |
| $C_{10}$ | 10.0 | 8.2 |
| $C_{20}$ | 7.8 | 9.4 |
| $C_{30}$ | 50.1 | 52.8 |
| $C_{40}$ | 25.2 | 23.7 |
| $C_{50}$ | 6.9 | 5.9 |
| $C_{30}/C_{40+}$ | 1.56 | 1.78 |

It is to be understood that the above disclosure is by way of specific example and that numerous modifications and variations are available to those of ordinary skill in the art without departing from the true spirit and scope of the invention.

We claim:

1. A process for producing a mixture of olefin oligomers which comprises contacting in the liquid phase an olefin having from about six to about 20 carbon atoms or a mixture thereof with a catalyst comprising boron trifluoride and a cocatalyst comprising between about 75 and about 99 weight percent of an aliphatic alcohol having from one to about ten carbon atoms, and between about one and about 25 percent of a polyol selected from ethylene glycol, propylene glycol, butane diol and glycerine.

2. A process for producing a mixture of olefin oligomers in accordance with claim 1 wherein the olefin is an alpha-olefin having between about ten and about 14 carbon atoms or a mixture thereof.

3. A process for producing a mixture of olefin oligomers in accordance with claim 1 wherein the partial pressure of the boron trifluoride is between about five and about 500 psig, the cocatalyst mixture comprises between about 0.01 and about 3.0 weight percent of said olefin, and the temperature is between about $-20°$ C. and about 90° C.

4. A process for producing a mixture of olefin oligomers in accordance with claim 1 wherein the cocatalyst comprises between about 85 and about 98 percent of the aliphatic alcohol, and between about two and about 15 percent of the polyol.

5. A process for producing a mixture of olefin oligomers in accordance with claim 4 wherein the aliphatic alcohol contains from about two to about 4 carbon atoms, and the polyol is ethylene glycol or propylene glycol.

6. A process for producing a mixture of olefin oligomers in accordance with claim 1 wherein the partial pressure of the boron trifluoride is between about 20 and about 100 psig, the cocatalyst mixture comprises between about 0.1 and about 1.0 weight percent of said olefin, and the temperature is between about 20° C. and about 70° C.

7. A process for producing a mixture of olefin oligomers in accordance with claim 1 wherein the olefin comprises 1-decene.

8. A process for producing a mixture of olefin oligomers in accordance with claim 4 wherein the alcohol is n-butanol.

* * * * *